US009167984B2

(12) United States Patent
Vondra et al.

(10) Patent No.: US 9,167,984 B2
(45) Date of Patent: Oct. 27, 2015

(54) DEVICE FOR BLOOD FLOW PROPERTY MEASUREMENT AND METHOD OF ITS CONNECTION

(75) Inventors: Vlastimil Vondra, Brno (CZ); Pavel Jurak, Brno (CZ); Josef Halamek, Brno (CZ); Ivo Viscor, Brno (CZ)

(73) Assignee: INSTITUTE OF SCIENTIFIC INSTRUMENTS AS CR, V. V. I., Brno (CZ)

( * ) Notice: Subject to any disclaimer, the term of this patent is extended or adjusted under 35 U.S.C. 154(b) by 83 days.

(21) Appl. No.: 13/132,265

(22) PCT Filed: Dec. 10, 2009

(86) PCT No.: PCT/CZ2009/000149
§ 371 (c)(1),
(2), (4) Date: Jun. 1, 2011

(87) PCT Pub. No.: WO2010/069276
PCT Pub. Date: Jun. 24, 2010

(65) Prior Publication Data
US 2011/0237966 A1    Sep. 29, 2011

(30) Foreign Application Priority Data

Dec. 15, 2008    (CZ) .............................. PV 2008-802

(51) Int. Cl.
*A61B 5/02*    (2006.01)
*A61B 5/053*    (2006.01)
*A61B 5/026*    (2006.01)

(52) U.S. Cl.
CPC ................. *A61B 5/053* (2013.01); *A61B 5/026* (2013.01)

(58) Field of Classification Search
USPC ................................................ 600/480–575
See application file for complete search history.

(56) References Cited

U.S. PATENT DOCUMENTS

| 5,505,209 | A | * | 4/1996 | Reining | 600/547 |
| 5,685,316 | A | * | 11/1997 | Schookin et al. | 600/526 |
| 2003/0135131 | A1 | * | 7/2003 | Scholz | 600/547 |
| 2004/0186392 | A1 | * | 9/2004 | Ward et al. | 600/547 |
| 2005/0070805 | A1 | * | 3/2005 | Dafni | 600/492 |
| 2008/0009757 | A1 | * | 1/2008 | Tsoglin et al. | 600/506 |
| 2009/0216140 | A1 | * | 8/2009 | Skrabal | 600/509 |

OTHER PUBLICATIONS

Vondra V, Halamek J, Viscor I, Jurak P. Two-channel bioimpedance monitor for impedance cardiography. 2006. Conf Proc IEEE Eng Med Biol Soc. 2006;1:6061-3.*
Stanley AW Jr, Herald JW, Athanasuleas CL, Jacob SC, Sims SW, Bartolucci AA, Tsoglin AN. Multi-channel electrical bioimpedance: a new noninvasive method to simultaneously measure cardiac and peripheral blood flow. Dec. 2007. Journal of Clinical Monitoring and Computing. vol. 21, Issue 6, pp. 345-351.*

* cited by examiner

*Primary Examiner* — Michael Kahelin
*Assistant Examiner* — Mitchell E Alter
(74) *Attorney, Agent, or Firm* — Notaro, Michalos & Zaccaria P.C.

(57) ABSTRACT

The device for blood flow property measurement in the body and the method of its connection to the subject enables to measure electrical impedance in the main parts of body simultaneously. The impedance is spatially localized in the particular scanning channels (5) both by the placement of the current electrodes (9) of the alternating current source (2) and by setting their frequencies, and by proper spatial placement of the voltage electrodes (6). For the purpose of the whole body measurement at least three current generators (1) and twelve scanning channels (5) are used. The number of scanning channels (5) can be adjusted as necessary. By means of this device it is possible to monitor blood pulse waves or blood flow in the particular parts of human body.

7 Claims, 3 Drawing Sheets

DEVICE FOR BLOOD FLOW PROPERTY MEASUREMENT AND METHOD OF ITS CONNECTION

FIELD OF THE INVENTION

The device for blood flow property measurement and method of its connection to a subject enables measuring of the electrical impedance on more parts of the body simultaneously.

BACKGROUND OF THE INVENTION

Nowadays one of the methods used for measuring the cardiac output is based on measuring the thorax impedance. Commercial devices are equipped with one or two scanning channels, not enabling to assess more parameters on more body parts simultaneously. Therefore it is not possible to monitor the pressure waves of the blood or the blood flow in various parts of human body simultaneously.

DESCRIPTION OF THE INVENTION

The device for measuring the blood flow property in a body and method of its connection to the body enable impedance measuring on more body parts simultaneously. The device measures the impedance by means of the multi-channel four-clamp method on all important body parts simultaneously, so that the impedance is localized spatially in the separate channels. This is done by using electrodes of an alternating-current source and choosing their proper frequencies on one hand, and by an appropriate placement of the voltage electrodes on the other hand. An advantage of the simultaneous independent impedance measurement in various body parts is the ability of monitoring and evaluating the trend of the desired parameters that can be derived from the impedance measured in various parts of body. It is thus possible to monitor the blood pressure wave or the blood flow in various parts of the human body.

The device consists of current generators comprising harmonic-signal generators with adjustable frequency and alternating-current sources with adjustable amplitude. The current clamps coming out from the alternating-current source are connected to the relevant body parts by electrodes. The reference frequency is led off from the harmonic-signal generator. The device can include an arbitrary number of current generators as independent alternating-current sources with relevant adjustable frequencies; their minimum number being three. The reference frequencies' values differ not less than by the width of the range transmitted by the scanning channel. To keep similar measurement conditions, they should lie as close to each other as possible (e.g. $f_1=49$ kHz, $f_2=50$ kHz and $f_3=51$ kHz). Further, the device includes the desired number of scanning channels which enable the detection only of those signals only, the frequency of which is adjusted. The scanning channel consists of two voltage electrodes, an amplifier with adjustable amplification, and a synchronous detector attached to the relevant reference frequency. The synchronous detector can be realized digitally, the reference frequencies can be generated inside the detector. The voltage electrodes of the scanning channels are placed on the body according to the places of interest. The voltage electrodes neighboring each other in a section can be replaced by one electrode. The measured voltage from the voltage electrodes is processed in the scanning channels in the digital or analogue way so that the output quantity corresponds with the voltage for the particular measured section on the given reference frequency. The impedance is then set according to the relation $Z=U/I$. The time flow of the impedance can be measured in chosen body parts. The outputs of each scanning channel is the instant impedance amplitude, the impedance phase and/or the real and imaginary part of the impedance. A control of the whole device, the communication between the various parts of the device and possible processing of the measured data are ensured by the control and processing block. There are outputs connected to the control and processing block. These are: a display, a control board (e.g. a keyboard), a positioning device, a printer, an analogue output, and a data link. The display, control board (e.g. a keyboard), and positioning device serve for communication with the operator and for displaying the desired outputs. The analogue output includes output connectors for separate measured and processed signals, especially the absolute impedance value, the impedance phase, and the real and imaginary part of the impedance. The data link makes possible a digital-data connection of the device to another computer or to a computer network, using either a metallic or a nonmetallic connection. By way of this connection the device can be controlled and the measured data processed by other computers.

The observed impedance as well as its absolute value, its real part, its imaginary part, or the phase in the particular body part are then processed in usual ways of evaluating the blood flow in the given body part or of other evaluations, e.g. assessing the amount of fluids or fat in the particular section.

The measuring device can operate independently or as a part of a measuring system which analyzes the measured impedances and assesses the desired biological parameters.

FIGURES

Figure 1:
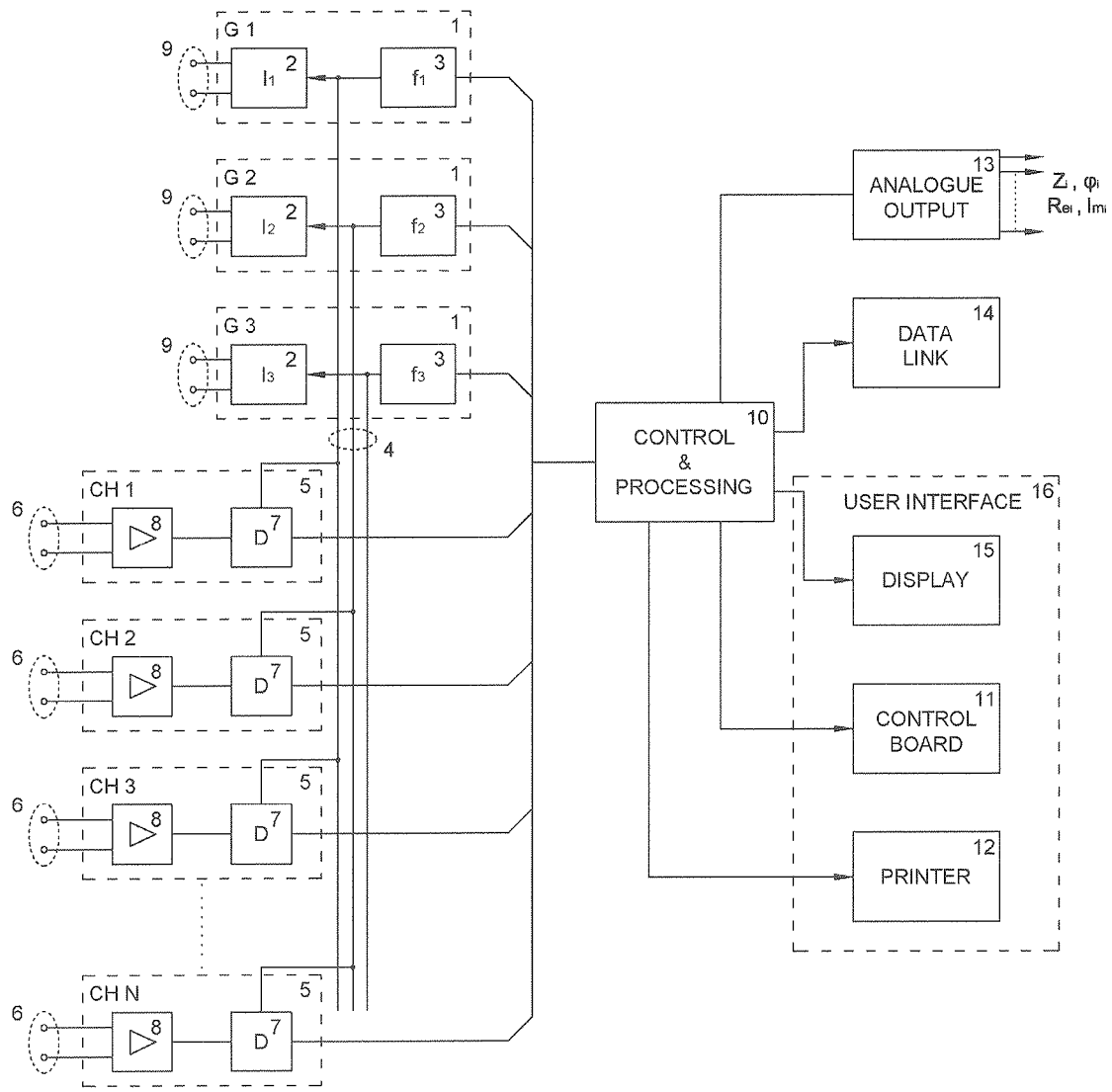
FIG. 1 shows a block diagram of the device for a simultaneous multi-channel measurement of the body impedance.
Figure 2:
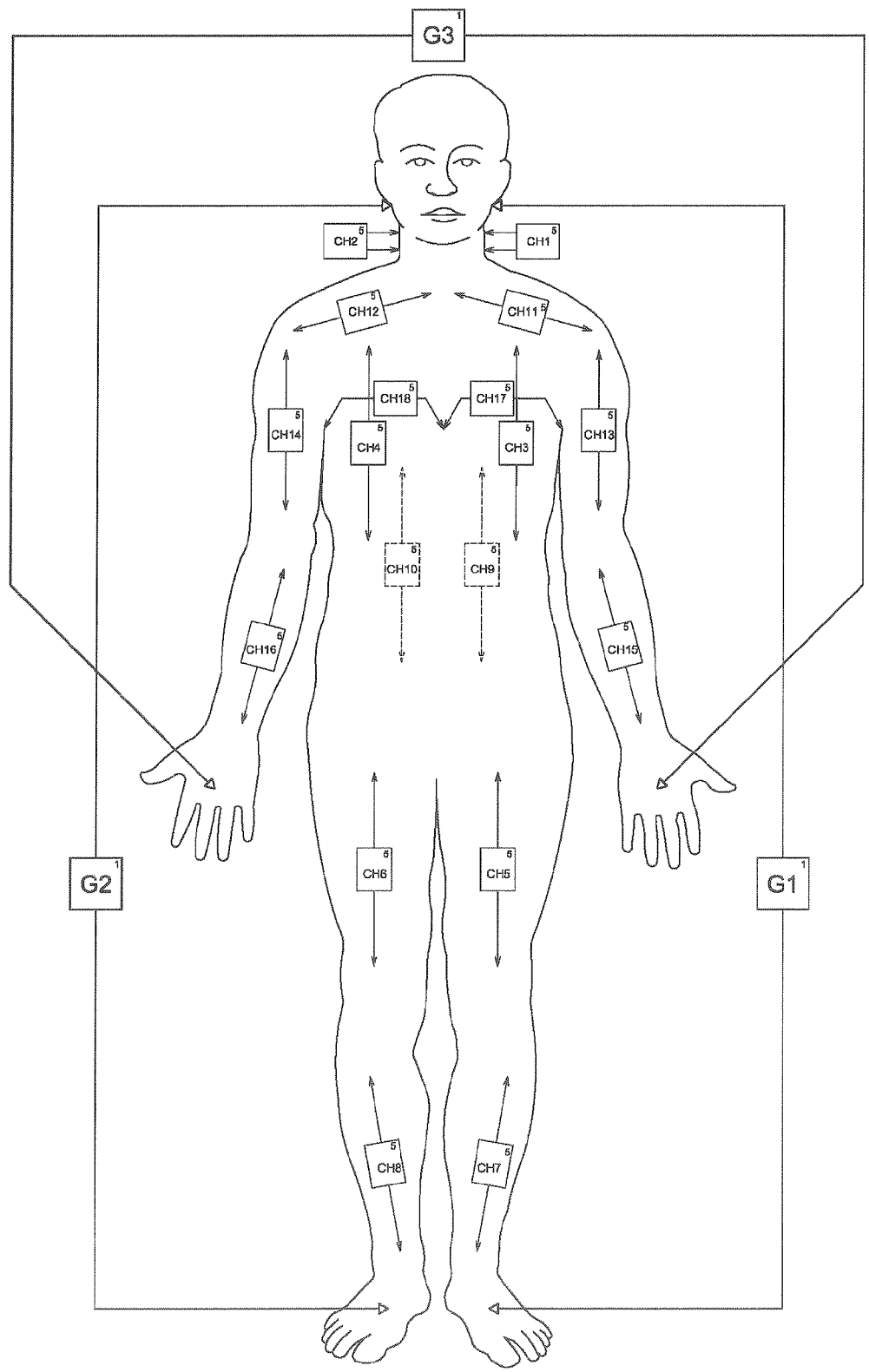
FIG. 2 shows the possibility of placement and connection of the current and voltage electrodes on human body for the purpose of monitoring the blood circulation in the whole body.
Figure 3:
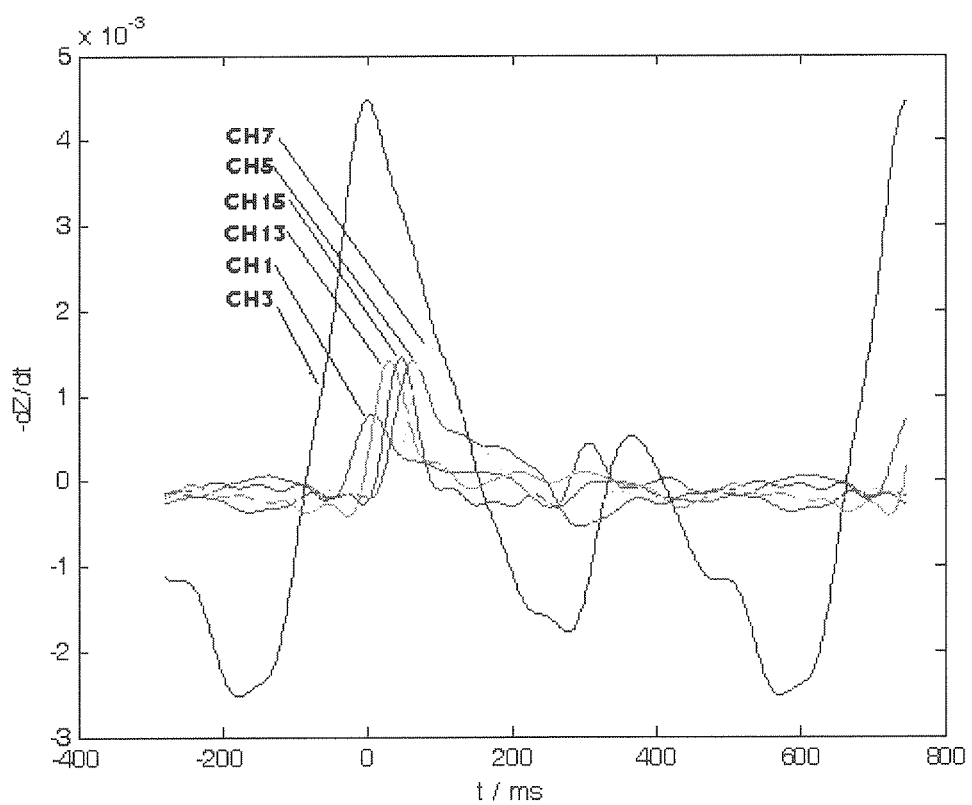

FIG. 3 presents an example of a time diagram for one heart beat, showing the time dependence of the impedance derivative, measured in all major left body parts—see the example below.

EXAMPLES

The device consisted of three current generators 1, comprising three alternating-current sources 2 and three harmonic-signal generators 3. From each harmonic-signal generator 3 a corresponding reference frequency link 4 was led off. Each harmonic-signal generator 3 was further connected to the control and processing block 10 and to the alternating-current source 2. Two current electrodes 9 were connected to each alternating-current source 2. Eighteen scanning channels 5 were connected to the corresponding reference-frequency link 4 through the relevant detector 7 which was further connected to the respective amplifier 8 and to the control and processing block 10. Two voltage electrodes 6 were connected to each amplifier 8. Some more outputs were connected to the control and processing block 10: the display 15, the control board 11, the printer 12, the analogue output 13 and the data link 14. The display 15, the control board 11, and the printer 12 form together the user interface 16.

The current source 2 $I_1=1$ mA with the frequency $f_1=49$ kHz was intended to measure the impedance of the left side of the body. One of its current electrodes 9 was attached to the head above the first scanning point behind the left ear, the other current electrode 9 was attached below the last scanning point on the left-foot instep. The $I_1$ current flowed from the left ear through the chest into the left leg down to the instep.

The current source 2 $I_2$=1 mA with the frequency $f_2$=50 kHz was intended to measure the impedance of the right side of the body. One of its current electrodes 9 was attached to the head above the first scanning point behind the right ear, the other current electrode 9 was attached below the last scanning point on the right-foot instep. The $I_2$ current flowed thus from the right ear through the chest into the right leg down to the instep.

The current source 2 $I_3$=1 mA with the frequency $f_3$=51 kHz was intended to measure the impedance of the upper limbs and the upper and middle part of the chest. One of the current electrodes 9 was attached before the first scanning point on the back of the left hand, the other current electrode 9 was attached after the last scanning point on the back of the right hand. The $I_3$ current flowed thus from the left palm through the left arm and the chest into the right arm down to its palm.

In this example 18 scanning channels 5 were used (CH1-CH18), the voltage electrodes 6 of them were placed in the following way:

The Left Part of the Body Downwards:
CH1: left carotid artery, electrode 1 being placed exactly under the ear, electrode 2 on the neck over the clavicle
CH3: left part of the chest, electrode 1 under the clavicle, electrode 2 under the rib cage
CH5: left thigh, electrode 1 above the groin, electrode 2 below the knee
CH7: left calf, electrode 1 below the knee, electrode 2 on the inner part of the calf above the ankle
CH9: left part of the belly and the belly artery—the electrodes being placed on the back on the left from the spinal column—electrode 1 at the level of the T9 vertebra, electrode 2 of the L5 vertebra The scanning channels 5 (CH1, CH3, CH5, CH7, CH9) were set at the frequency $f_1$=49 kHz.

The Right Part of the Body Downwards:
CH2: right carotid artery, electrode 1 being placed exactly under the ear, electrode 2 on the neck over the clavicle
CH4: right part of the chest, electrode 1 under the clavicle, electrode 2 under the rib cage
CH6: right thigh, electrode 1 above the groin, electrode 2 below the knee
CH8: right calf, electrode 1 below the knee, electrode 2 on the inner part of the calf above the ankle
CH10: right part of the belly and the belly artery—the electrodes being placed on the back on the right from the spinal column—electrode 1 at the level of the T9 vertebra, electrode 2 of the L5 vertebra The scanning channels 5 (CH2, CH4, CH6, CH8, CH10) were set at the frequency $f_2$=50 kHz.

Upper Limbs and Chest:
CH11: left upper part of the chest, electrode 1 in the left armpit, electrode 2 under the larynx
CH13: left arm, electrode 1 on the inner side of the elbow, electrode 2 in the left armpit
CH15: left forearm, electrode 1 on the inner side of the forearm over the palm, electrode 2 on the inner side of the elbow
CH12: right upper part of the chest, electrode 1 in the right armpit, electrode 2 under the larynx
CH14: right arm, electrode 1 on the inner side of the elbow, electrode 2 in the right armpit
CH16: right forearm, electrode 1 on the inner side of the forearm over the palm, electrode 2 on the inner side of the elbow
CH17: left part of the chest at the level of the heart, electrode 1 in the left armpit, electrode 2 under the sternum
CH18: right part of the chest at the level of the heart, electrode 1 under the sternum, electrode 2 in the right armpit The scanning channels 5 (CH11, CH12, CH13, CH14, CH15, CH16, CH17, CH18) were set at the frequency $f_3$=51 kHz.

The bandwidth of all scanning channels was 250 Hz.

Industrial Applicability

The device can be utilized in medical and related branches, e.g. in medical appliances and patients' monitors for analyzing blood circulation and its dynamic characteristic predominantly. The device is utilizable in the field of analyzing properties of human-body parts in particular. The properties can be derived from the electrical impedance of the body part or its changes.

The invention claimed is:

1. A device for blood flow property measurement comprising:
   three current generators (1);
   at least twelve scanning channels (5);
   at least six current electrodes (9);
   at least three reference-frequency links (4);
   a control and processing block (10); and
   a data link (14) connected to at least one member of the group consisting of a personal computer (PC), a computer network, a computer network and display (15), and a display (15); and
   a control board (11),
   wherein each current generator (1) contains an alternating-current source (2) and a harmonic-signal generator (3) linked to the alternating-current source (2),
   wherein each scanning channel (5) contains an amplifier (8), a detector (7) and at least two voltage electrodes (6), two of the at least six current electrodes (9) are attached to each alternating-current source (2),
   wherein each harmonic-signal generator (3) is connected to at least four scanning channels (5) by means of a reference-frequency link (4) through a detector (7) which is connected to an amplifier (8),
   wherein each amplifier (8) has two of the voltage electrodes (6) connected to thereto,
   wherein each harmonic-signal generator (3) and each detector (7) is connected to the control and processing block (10) to which additional outputs are attached,
   wherein the data link (14) is connected to at least one member of the group consisting of a personal computer (PC), a computer network, a computer network and display (15), and a display (15) and further connected to the control board (11); and
   wherein the current generators (3) have reference frequency values differing from one another by about 1 Khz.

2. The device for blood flow property measurement according to claim 1, wherein at the least six current electrodes (9) are adapted to be placed on the body so that there are at least six current electrodes (9) applicable for placing on the body, organized as three pairs of current electrodes (9), each pair of current electrodes (9) being connected to the alternating current source (2), the frequency of which differs from the frequency of any other alternating current source (2) connected to the pair of current electrodes (9) by at least a bandwidth of the signal transmitted through the scanning channel (5), and wherein every circuit comprises at least eight voltage electrodes (6), organized as four pairs of voltage electrodes (6).

3. The device for blood flow property measurement according to claim 2, wherein a first alternating-current circuit is adapted to be led through the left part of the body from the left part of the head to the instep of the left foot, a second alternating-current circuit is adapted to be led through the right part of the body from the right part of the head to the instep of the right foot and a third alternating current circuit is adapted to be led through the upper limbs and the chest from the left palm through the chest to the right palm.

4. The device for blood flow property measurement according to claim 3, wherein the voltage electrodes (6) in a circuit adapted to be led through the left part of the body are adapted to be placed on the left part of the neck, left part of the chest, left thigh, and left calf, the voltage electrodes (6) in a circuit adapted to be led through the right part of the body are adapted to be placed on the right part of the neck, right part of the chest, right thigh, and right calf, and the voltage electrodes (6) in the circuit adapted to be led through the upper limbs and the chest are adapted to be placed on the left arm, left forearm, right arm, and right forearm.

5. The device for blood flow property measurement according to claim 1, wherein the control and processing block (10) contains an analogue output (13).

6. The device for blood flow property measurement according to claim 1, wherein the control and processing block (10) is connected to a printer (12).

7. The device for blood flow property measurement according to claim 1, wherein the current generators have reference frequency values of 49 kHz, 50 kHz and 51 kHz, respectively.

* * * * *